(12) United States Patent
Hancock et al.

(10) Patent No.: US 12,239,368 B2
(45) Date of Patent: Mar. 4, 2025

(54) ELECTROSURGICAL INSTRUMENT

(71) Applicant: CREO MEDICAL LIMITED, Chepstow (GB)

(72) Inventors: Christopher Paul Hancock, Chepstow (GB); George Ullrich, Bangor (GB); Shaun Preston, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 912 days.

(21) Appl. No.: 17/294,637

(22) PCT Filed: Nov. 28, 2019

(86) PCT No.: PCT/EP2019/082885
§ 371 (c)(1),
(2) Date: May 17, 2021

(87) PCT Pub. No.: WO2020/114878
PCT Pub. Date: Jun. 11, 2020

(65) Prior Publication Data
US 2022/0008129 A1    Jan. 13, 2022

(30) Foreign Application Priority Data

Dec. 3, 2018    (GB) ...................................... 1819683

(51) Int. Cl.
*A61B 18/18*    (2006.01)
*A61B 18/14*    (2006.01)
(Continued)

(52) U.S. Cl.
CPC ..................... *A61B 18/1815* (2013.01); *A61B 2017/00185* (2013.01); *A61B 2017/0019* (2013.01);
(Continued)

(58) Field of Classification Search
CPC ........... A61B 2018/00613; A61B 2018/00785; A61B 2018/00904; A61B 2018/1869; A61B 2018/1823; A61B 2018/1861
See application file for complete search history.

(56) References Cited

U.S. PATENT DOCUMENTS

2006/0293651 A1\*  12/2006  Cronin ................... A61B 18/18
                                                    607/101
2007/0191825 A1\*  8/2007  Cronin ............... A61B 18/1815
                                                    607/101
(Continued)

FOREIGN PATENT DOCUMENTS

EP    2 008 604 A2    12/2008
EP    2 060 239 A1    5/2009
(Continued)

OTHER PUBLICATIONS

International Preliminary Report on Patentability issued from the International Preliminary Examining Authority in counterpart International Application No. PCT/EP2019/082885, mailed on Feb. 5, 2021.
(Continued)

*Primary Examiner* — Jaymi E Della
(74) *Attorney, Agent, or Firm* — ArentFox Schiff LLP (57) ABSTRACT

An electrosurgical instrument having a radiating tip portion capable performing tissue ablation using microwave energy and electroporation (e.g. non-thermal irreversible electroporation) in a minimally invasive manner. The electrosurgical instrument may be used to perform microwave ablation and electroporation separately (e.g. sequentially) or simultaneously. The radiating tip portion may be dimensioned to be suitable for insertion into a pancreas via a surgical scoping device, to provide a rapid and accurate alternative to known RF ablation techniques. By enabling tumours within the pancreas to be treated using a minimally invasive procedure,
(Continued)

it may be a viable option to use ablation and/or electroporation treatment for both curative as well as palliative reasons.

21 Claims, 9 Drawing Sheets (51) Int. Cl.
*A61B 17/00* (2006.01)
*A61B 18/00* (2006.01)

(52) U.S. Cl.
CPC .............. *A61B 2017/00867* (2013.01); *A61B 2018/0013* (2013.01); *A61B 2018/00178* (2013.01); *A61B 2018/00577* (2013.01); *A61B 2018/00613* (2013.01); *A61B 2018/00982* (2013.01); *A61B 2018/1869* (2013.01)

(56) References Cited

U.S. PATENT DOCUMENTS

| | | | |
|---|---|---|---|
| 2008/0033422 A1 | 2/2008 | Turner et al. | |
| 2008/0045938 A1* | 2/2008 | van der Weide | A61B 18/1815 606/33 |
| 2009/0326620 A1 | 12/2009 | Rossetto et al. | |
| 2010/0023004 A1* | 1/2010 | Francischelli | A61B 18/1492 606/41 |
| 2010/0145328 A1* | 6/2010 | Hancock | A61B 18/1815 606/33 |
| 2010/0152725 A1* | 6/2010 | Pearson | A61B 18/1815 606/41 |
| 2012/0209257 A1* | 8/2012 | van der Weide | A61B 18/1815 606/41 |
| 2012/0310230 A1 | 12/2012 | Willis | |
| 2013/0211176 A1 | 8/2013 | Habib | |
| 2014/0005655 A1* | 1/2014 | Brannan | H01Q 1/42 29/600 |
| 2014/0031811 A1* | 1/2014 | Brannan | A61B 18/1815 607/101 |
| 2015/0250540 A1* | 9/2015 | Behdad | A61B 18/1815 606/33 |
| 2015/0313670 A1* | 11/2015 | Shroff | A61B 18/1815 606/33 |

FOREIGN PATENT DOCUMENTS

| | | | | |
|---|---|---|---|---|
| EP | 3 389 536 A1 | 10/2018 | | |
| JP | 2010-088884 A | 4/2010 | | |
| JP | 2011-41799 A | 3/2011 | | |
| JP | 2018-530360 A | 10/2018 | | |
| WO | WO-2017103209 A1 * | 6/2017 | ......... A61B 18/1492 |
| WO | WO-2017174513 A1 * | 10/2017 | ............. A61B 1/018 |
| WO | WO 2018/202758 A1 | 11/2018 | | |

OTHER PUBLICATIONS

International Search Report and Written Opinion, issued by International Searching Authority in corresponding International Application No. PCT/EP2019/082885, mailed on Apr. 6, 2020.

Search Report under Section 17(5), issued by the United Kingdom Intellectual Property Office in counterpart United Kingdom Application No. GB1819683.2, dated May 9, 2019.

Written Opinion of the International Preliminary Examining Authority, issued by the International Preliminary Examining Authority in corresponding International Application No. PCT/EP2019/082885, mailed on Aug. 14, 2020.

* cited by examiner

ELECTROSURGICAL INSTRUMENT

CROSS-REFERENCE TO RELATED APPLICATIONS

This application is a National Stage entry of International Application No. PCT/EP2019/082885, filed on Nov. 28, 2019, which claims priority to United Kingdom Patent Application No. 18196832, filed on Dec. 3, 2018. The disclosures of the priority applications are hereby incorporated in their entirety by reference.

FIELD OF THE INVENTION

The invention relates to an electrosurgical instrument for delivering electromagnetic energy to biological tissue in order to ablate target tissue. In particular, the probe is configured to be insertable through a channel of a surgical scoping device or catheter that can be introduced to a treatment site in a non-invasive manner. The probe may be arranged to ablate tissue, such as a tumour, cyst or other lesion. The probe may be particularly suited for treatment in the pancreas.

BACKGROUND TO THE INVENTION

Electromagnetic (EM) energy, and in particular microwave and radiofrequency (RF) energy, has been found to be useful in electrosurgical operations, for its ability to cut, coagulate, and ablate body tissue. Typically, apparatus for delivering EM energy to body tissue includes a generator comprising a source of EM energy, and an electrosurgical instrument connected to the generator, for delivering the energy to tissue. Conventional electrosurgical instruments are often designed to be inserted percutaneously into the patient's body. However, it can be difficult to locate the instrument percutaneously in the body, for example if the target site is in a moving lung or a thin walled section of the gastrointestinal (GI) tract. Other electrosurgical instruments can be delivered to a target site by a surgical scoping device (e.g. an endoscope) which can be run through channels in the body such as airways or the lumen of the oesophagus or colon. This allows for minimally invasive treatments, which can reduce the mortality rate of patients and reduce intraoperative and postoperative complication rates.

Tissue ablation using microwave EM energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating.

This principle is harnessed in microwave ablation therapies, where water molecules in target tissue are rapidly heated by application of a localised electromagnetic field at microwave frequencies, resulting in tissue coagulation and cell death. It is known to use microwave emitting probes to treat various conditions in the lungs and other organs. For example, in the lungs, microwave radiation can be used to treat asthma and ablate tumours or lesions.

Another type of tumour treatment makes use of an effect known as electroporation (or electropermeabilization). In this technique, electrical pulses are applied to biological tissue to cause nanoscale pores to open in cell membranes at a target site. The pores permit anticancer drugs or other material that cannot normally permeate through the cell membrane to enter the cells. The pores may then reseal to trap the material within the cell, where it may cause a therapeutic effect (e.g. to kill the cell). It is also known to use electroporation to create permanent nanoscale pores in the cell membrane. These pores do not reseal, and thus disrupt cell homeostasis, eventually leading to cell death. This technique is known as irreversible electroporation or non-thermal irreversible electroporation. Unlike thermal ablation, e.g. using microwave energy, irreversible electroporation preserves the extracellular matrix.

A technique of treating tissue in the pancreas using endoscopic ultrasound guided radiofrequency ablation is known (Pai, M., et al.: *Endoscopic ultrasound guided radiofrequency ablation, for pancreatic cystic neoplasms and neuroendocrine tumors*, World J Gastrointest Surg 2015 Apr. 27; 7(4): 52-59). In this technique a conductive wire having a small diameter (e.g. 0.33 mm) is inserted through the working channel of an ultrasound-enabled endoscope. RF power is applied to the wire in conjunction with an external grounded return pad in contact with the patient's skin to coagulate tissue in the liver and pancreas. To ablate lesions it is necessary to apply power for 90-120 seconds, and, in some cases to remove and reposition the wire.

SUMMARY OF THE INVENTION

At its most general, the invention provides an electrosurgical instrument having a radiating tip portion capable performing tissue ablation using microwave energy and electroporation (e.g. non-thermal irreversible electroporation) in a minimally invasive manner. The electrosurgical instrument may be used to perform microwave ablation and electroporation separately (e.g. sequentially) or simultaneously. The radiating tip portion may be dimensioned to be suitable for insertion into a pancreas via a surgical scoping device, to provide a rapid and accurate alternative to known RF ablation techniques. By enabling tumours within the pancreas to be treated using a minimally invasive procedure, it may be a viable option to use ablation and/or electroporation treatment for both curative as well as palliative reasons.

Although the invention may find particular use in the pancreas, it may also be suitable for use in other awkward treatment sites, such as the lungs, etc. The instrument structure disclosed herein enables the radiating tip portion to be provided with appropriate length and rigidity for use in a variety of settings.

By combining the ability to perform microwave ablation and electroporation with the same instrument, it is possible to rapidly change between treatment modalities during an electrosurgical procedure without having to change instruments. Microwave ablation and electroporation may be used in a complimentary manner, in order to treat target tissue more effectively and/or minimise treatment time. Due to the small diameter of the radiating tip portion, the radiating tip portion may heat up when it is used to deliver microwave energy into tissue. Excessive heating may cause damage to healthy surrounding tissue, so it is often necessary to wait after application of microwave energy for the radiating tip portion to cool back down. With the instrument of the invention, it is possible to alternate between treatment with microwave energy and electroporation, in order to avoid excessive heating of the radiating tip portion. This may enable the overall treatment time to be minimised.

According to an embodiment of the invention, there is provided an electrosurgical instrument comprising: a coaxial cable configured to convey microwave energy; a rod-shaped radiating tip portion extending in a longitudinal direction away from a distal end of the coaxial cable, wherein the radiating tip portion comprises: a proximal coaxial transmission line for receiving and conveying the microwave energy, the proximal coaxial transmission line including an inner conductor, an outer conductor and a dielectric material separating the inner conductor from the outer conductor; and a distal needle tip mounted at a distal end of the proximal coaxial transmission line, the distal needle tip comprising a rigid dielectric sleeve that extends the longitudinal direction from a distal end of the proximal coaxial transmission line, wherein the rod-shaped radiating tip portion has a diameter less than a diameter of the coaxial cable, wherein the rigid dielectric sleeve surrounds an elongate conductive element that is electrically connected to the inner conductor of the proximal coaxial transmission line and extends beyond a distal end of the outer conductor of the proximal coaxial transmission line, wherein the elongate conductive element is configured to operate as a half wavelength transformer for the microwave energy to thereby radiate the microwave energy from the distal needle tip into biological tissue, wherein the elongate conductive element terminates at an active electrode exposed on a distal end of distal needle tip, and wherein the active electrode is axially spaced from a return electrode that is electrically connected to the distal end of the outer conductor of the proximal coaxial transmission line, the active electrode and return electrode be configured to establish an electric field for electroporation of biological tissue at the distal needle tip.

The distal needle tip may be configured as a half wavelength transformer if its electrical length corresponds to a half wavelength of the microwave energy. An advantage of configuring the distal needle tip as a half wavelength transformer is to minimise reflections at the interface between components, e.g. between the coaxial cable and proximal coaxial transmission line, and between the proximal coaxial transmission line and the distal needle tip. A reflection coefficient at the latter interface is typically larger due to a larger variation in impedance. The half wavelength configuration minimises these reflections so that the dominant reflection coefficient becomes that of the interface between the proximal coaxial transmission line and the tissue. The impedance of the proximal coaxial transmission line may be selected to be identical or close to the expected tissue impedance to provides a good match at the frequency of the microwave energy.

As a result of the configuration of the radiating tip portion, the impedance of the coaxial transmission line may be 'seen' by the tissue rather than the (smaller) impedance of the distal needle tip structure. The physical length of the distal needle tip need not (indeed probably will not) correspond to a half wavelength of the microwave energy in free space, because the shape of distal needle tip and its interaction with the proximal coaxial transmission line can be selected to control the physical length of the distal needle tip whilst enabling it to operate electrically as a half wavelength transformer.

The coaxial cable may be configured to convey an electroporation signal which, when received by the rod-shaped radiating tip portion, establishes the electric field for electroporation of biological tissue at the distal needle tip. The active electrode may be disposed at a surface of the distal needle tip.

The electroporation waveform may comprise one or more high voltage energy pulses configured to open pores in cell membranes. The invention may be used in a scenario where a therapeutic agent is present at a treatment site, whereby opening pores in the cell membrane facilitates or enables the therapeutic agent to enter the cells. In other words, the invention may be used in conventional electroporation procedures.

Alternatively or additionally, the energy for electroporation may be configured to permanently open pores, thereby to cause irreversible disruption to the cell membrane causing the cells to die. In other words, the instrument can be used for irreversible electroporation (IRE).

The electroporation waveform may comprise one or more rapid high voltage pulses. Each pulse may have a pulse width in a range from 1 ns to 10 ms, preferably in the range from 1 ns to 100 µs, although the invention need not be limited to this range. Shorter duration pulses (e.g. equal to or less than 10 ns) may be preferred for reversible electroporation. For irreversible electroporation, longer duration pulses or more pulses may be used relative to reversible electroporation.

Preferably the rise time of each pulse is equal to or less than 90% of the pulse duration, more preferably equal to or less than 50% of the pulse duration, and most preferably equal to or less than 10% of the pulse duration. For the shorter pulses, the rise time may be of the order of 100 ps. In some examples, the electroporation waveform may be a radiofrequency (RF) or low frequency electromagnetic signal.

Each pulse may have an amplitude in the range 10 V to 10 kV, preferably in the range 1 kV to 10 kV. Each pulse may be positive pulse from a ground potential, or a sequence of alternating positive and negative pulses from a ground potential.

The electroporation waveform may be a single pulse or a plurality of pulses, e.g. a period train of pulses. The waveform may have a duty cycle equal to or less than 50%, e.g. in the range 0.5% to 50%.

In one example, pulse widths of the order of 200 ms delivered in a series of 10 to 100 pulses may be used for irreversible electroporation. In one example, the electroporation waveform may comprise 10×300 µs pulses of amplitude 1.5 kV delivered three times with around 1 minute between delivery. This waveform can cause cell apoptosis or death in hepatocellular carcinoma.

The electroporation waveform may be delivered during a treatment period that is selected depending on the desired effect. For example, the treatment period may be short, e.g. less than 1 second, or a few seconds, or around 1 minute. Alternatively the treatment period may be longer, e.g. up to an hour.

The coaxial cable may be a conventional low loss coaxial cable that is connectable at a proximal end to an electrosurgical generator. The coaxial cable may have a centre conductor separated from an outer conductor by a dielectric material. The coaxial cable may further include an outer protective sheath for insulating and protecting the cable. In some examples, the protective sheath may be made of or coated with a non-stick material to prevent tissue from sticking to the cable. The radiating tip portion is located at the distal end of the coaxial cable, and is connected to receive the EM energy conveyed along the coaxial cable.

The proximal coaxial transmission line may be connected to the distal end of coaxial cable. In particular, the inner conductor and outer conductor of the proximal coaxial transmission line may be electrically connected to the centre conductor and the outer conductor of the coaxial cable, respectively. The materials used in the proximal coaxial transmission line may be the same or different to those used in the coaxial cable. The materials used in the proximal coaxial transmission line may be selected to provide a desired flexibility and/or impedance of the proximal coaxial transmission line. For example, the dielectric material of the proximal coaxial transmission line may be selected to improve impedance matching with target tissue.

The dimensions of the components of the proximal coaxial transmission line may be chosen to provide it with an impedance that is identical or close to the impedance of the flexible coaxial cable (e.g. around 50Ω). The inner conductor may be formed from a material with high conductivity, e.g. silver.

The radiating tip portion may be secured to the flexible coaxial cable by a collar mounted over a junction therebetween. The collar may be electrically conductive, e.g. formed from brass. It may electrically connect the outer conductor with an outer conductor of the flexible coaxial cable.

An outer diameter of the radiating tip portion is smaller than an outer diameter of the coaxial cable. This may facilitate insertion of the radiating tip portion into target tissue, and improve the manoeuvrability of the radiating tip portion. This configuration may be particularly suited to treatment of tumours in the pancreas, as it may facilitate insertion of the radiating tip portion into the pancreas through the duodenum wall.

The radiating tip portion may include a non-stick coating (e.g. made of PTFE), to prevent tissue from sticking to it. The non-stick coating may be formed from Parylene C or Parylene D. The non-stick coating may be formed along the whole length of the radiating tip portion except for the active and return electrodes, which are exposed to facilitate efficient delivery of the electroporation signal into tissue. The non-stick coating may be applied only along a length corresponding to an active zone of ablation, e.g. along a region extending 2 cm back from the distal end (except for the active and return electrodes). When the needle is only partially coated, the needle may be less susceptible to a build-up of thermal energy, which can cause the needle to heat up.

In some embodiments, the return electrode may be formed by a distal portion of the outer conductor of the proximal coaxial transmission line. In this manner, the radiating tip portion may act as a bipolar electroporation probe when it receives an electroporation waveform. By using the distal portion of the outer conductor as the return electrode, the electric field may be localised around the distal needle tip, so that electroporation may be performed in a region around the distal needle tip. The distal portion of the outer conductor may be located at the distal end of the proximal coaxial transmission line, adjacent to the distal needle tip. Where the outer conductor is formed from nitinol or some other flexible conductive material, the return electrode may include a coating formed on distal portion of the outer conductor of a material having a higher conductivity that the nitinol. The material may be silver, for example. To facilitate efficient delivery of the electroporation signal, the active and return electrodes may be polished, i.e. made as smooth as possible.

The elongate conductive element may radiate microwave energy along its length, to ablate tissue in a region located around the distal needle tip. In some cases, the elongate conductive element may be a distal portion of the inner conductor that extends into the distal needle tip.

The active electrode is electrically connected to the elongate conductive element. In this manner, the electroporation waveform may be delivered to the active electrode via the elongate conductive element. The active electrode may also serve to shape a microwave radiation profile of the radiating tip portion, e.g. to concentrate emission of microwave energy around the distal needle tip.

In some embodiments, the active electrode may be a conductive ring arranged concentrically with the elongate conductive element. In other words, a central axis of the conductive ring may be aligned with a longitudinal axis of elongate conductive element. This may serve to deliver the electroporation waveform to tissue symmetrically about the longitudinal axis. This may also serve to provide an axially symmetric microwave radiation profile.

The conductive ring may have a channel extending longitudinally therethrough, and a portion of the elongate conductive element may be contained within the channel. In this manner, the elongate conductor may be electrically connected to the active electrode inside the channel. A diameter of the channel may be dimensioned to substantially match an outer diameter of the elongate conductive element, so that the channel may form an interference fit around the elongate conductive element. This may serve to secure the active electrode relative to the elongate conductive element.

In some embodiments, the distal needle tip may comprise a tip element mounted at a distal end of the conductive ring to close a distal end of the channel. The tip element may be made of a dielectric material. The dielectric material of the tip element may be selected to improve impedance matching between the radiating tip portion and target tissue. A portion of the tip element may protrude within the channel, to hold the tip element in place relative to the channel.

A distal end of the tip element may be pointed (e.g. sharpened). This may facilitate insertion of the distal needle tip into target tissue. For example, this may facilitate insertion of the instrument through the duodenal or gastric wall into the pancreas.

The distal dielectric sleeve may have a bore formed therethrough for receiving the elongate conductive element. The distal dielectric sleeve may be made from a different material from the dielectric material in the proximal coaxial transmission line.

The distal dielectric sleeve may have a higher rigidity than the dielectric material of the proximal coaxial transmission line. Providing a higher rigidity to the distal dielectric sleeve may facilitate insertion of the distal needle tip into target tissue, whilst having a lower rigidity proximal coaxial transmission line may facilitate bending of the radiating tip portion. This may enable the instrument to be guided through narrow and winding passageways, whilst still enabling it to be inserted into target tissue. For example, the dielectric material of the proximal coaxial transmission line may be made of a flexible dielectric material (e.g. PTFE), and the distal dielectric sleeve may be made of e.g. a ceramic, polyether ether ketone (PEEK) or glass-filled PEEK. The tip element of the distal needle tip may be made of the same material as the distal dielectric sleeve.

In some embodiments, the distal dielectric sleeve may include zirconia. The inventors have found that zirconia provides a good rigidity for inserting the distal needle tip into tissue. Moreover, the inventors have found that using a zirconia distal dielectric sleeve may provide good impedance matching with target tissue.

In some embodiments, a distal portion of the outer conductor may overlay a proximal portion of the distal dielectric sleeve. In other words, the proximal portion of the distal dielectric sleeve may be contained within the distal portion of the outer conductor. This may serve to strengthen the connection between the distal needle tip and the proximal coaxial transmission line.

The length of the radiating tip portion where the distal portion of the outer conductor overlays the proximal portion of the distal needle tip may form an intermediate coaxial transmission line between the proximal transmission line and the distal needle tip. The intermediate coaxial transmission line may have a higher dielectric constant than the proximal coaxial transmission line to allow for a smaller physical length whilst getting the required electrical length (half wave). At microwave frequencies, a distal portion of the distal needle tip may act as an open-ended loaded monopole connected to the intermediate coaxial transmission line. The distal needle tip may also be considered as a single structure which ends in an open-ended co-axial monopole to shape the ablation zone.

In some embodiments, the distal dielectric sleeve may formed by a pair of cooperating parts, each one of the cooperating parts having a longitudinal groove formed in a surface thereof for receiving the elongate conductor. Such a structure of the distal dielectric sleeve may facilitate assembly of the radiating tip portion. When the cooperating parts are assembled to form the distal dielectric sleeve, the grooves in the cooperating parts may form a bore in which the elongate conductor is received. The cooperating parts may be secured together using an adhesive.

In some embodiments, the outer conductor of the proximal coaxial transmission line may be formed from nitinol. For example, the outer conductor may be formed of a nitinol tube. The inventors have found that nitinol exhibits a longitudinal rigidity sufficient to transmit a force capable of penetrating the duodenum wall. Additionally, the flexibility of nitinol may facilitate bending of the radiating tip portion, so that the instrument may be guided through narrow bending passageways. Forming the outer conductor of nitinol may thus facilitate use of the instrument for treatment of tumours in the pancreas.

A conductive outer layer may formed on an outer surface of the outer conductor, the conductive outer layer having a higher conductivity than nitinol. The conductive outer layer may serve to reduce losses of microwave energy in the radiating tip portion, to improve efficiency of microwave energy delivery to the distal needle tip. A thickness of the conductive outer layer may be smaller than a thickness of the nitinol, to minimise any impact of the conductive outer layer on flexibility of the radiating tip portion.

The radiating tip portion may have a length equal to or greater than 30 mm and preferably 40 mm, but could be as long as 100 mm. This length may enable access to treatment regions at all locations within the pancreas. The radiating tip portion may have a maximum outer diameter equal to or less than 1.2 mm. This may reduce or minimise the penetration hole cause by insertion of the instrument, so as not to cause an undue delay in healing. Minimising the size of the penetration hole may also avoid the undesirable situation of it healing open and causing a fistula or unwanted channel between the GI tract and the body cavity.

In some embodiments, the inner conductor may extend from a distal end of the flexible coaxial cable, the inner conductor being electrically connected to a centre conductor of the flexible coaxial cable, and the inner conductor may have a diameter that is less than the diameter of the centre conductor of the flexible coaxial cable. This may improve the flexibility of the radiating tip portion. For example, the diameter of the inner conductor may be 0.25 mm. The diameter of the inner conductor may take into account that the dominant parameter that determines loss (and heating) along the radiating tip portion is the conductor loss, which is a function of the diameter of the inner conductor. Other relevant parameters are the dielectric constants of the distal dielectric sleeve and dielectric material of the proximal coaxial transmission line, and the diameter and material used for the outer conductor.

The electrosurgical instrument discussed above may form part of a complete electrosurgical system. For example, the system may include an electrosurgical generator arranged to supply microwave energy and electromagnetic energy having an electroporation waveform; and the electrosurgical instrument of the invention connected to receive the microwave energy and electromagnetic energy having an electroporation waveform from the electrosurgical generator. The electrosurgical apparatus may further include a surgical scoping device (e.g. an endoscope) having a flexible insertion cord for insertion into a patient's body, wherein the flexible insertion cord has an instrument channel running along its length, and wherein the electrosurgical instrument is dimensioned to fit within the instrument channel.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less. In embodiments of the invention, the surgical scoping device may be an ultrasound-enabled endoscope.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate probe. In use, the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Preferred spot frequencies for microwave EM energy include: 915 MHz, 2.45 GHz, 3.3 GHz, 5.8 GHz, 10 GHz, 14.5 GHz and 24 GHz. 5.8 GHz may be preferred. The device may deliver energy at more than one of these microwave frequencies.

The term "radiofrequency" or "RF" may be used to indicate a frequency between 300 kHz and 400 MHz. The term "low frequency" or "LF" may mean a frequency in the range 30 kHz to 300 kHz.

BRIEF DESCRIPTION OF THE DRAWINGS

Embodiments of the invention are discussed below with reference to the accompanying drawings, in which.

DETAILED DESCRIPTION; FURTHER OPTIONS AND PREFERENCES

Figure 1:
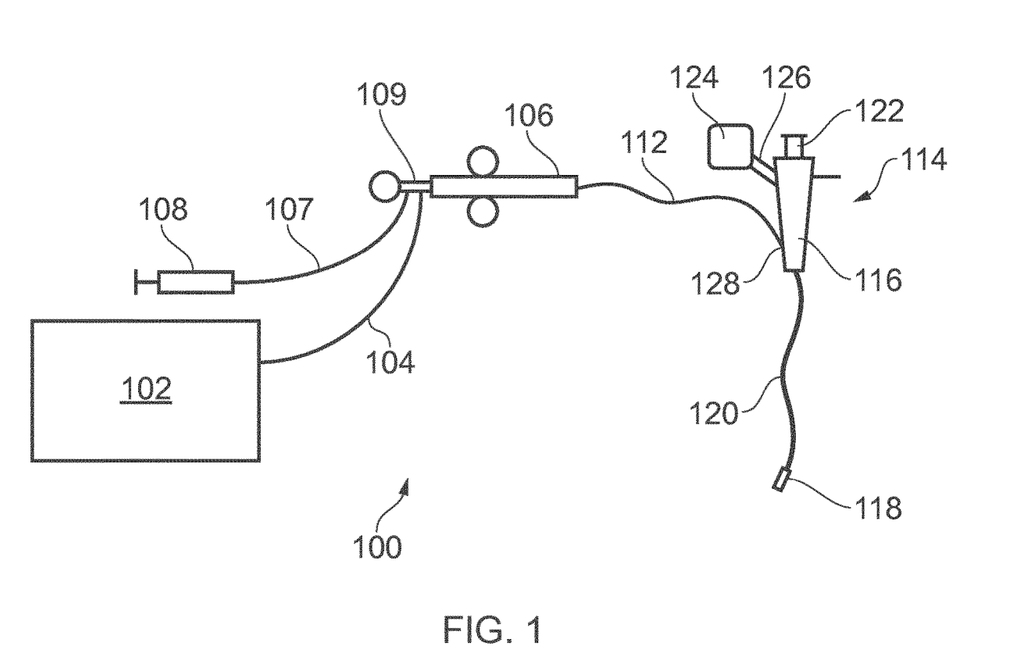
FIG. 1 is a schematic diagram of an electrosurgical system for tissue ablation that is an embodiment of the invention.

FIG. 1 is a schematic diagram of an electrosurgical ablation apparatus 100 that is capable of supplying microwave energy and energy for electroporation to the distal end of an invasive electrosurgical instrument. The system 100 comprises a generator 102 for controllably supplying microwave energy and energy for electroporation. Energy for electroporation may comprise pulsed or sinusoidal (e.g. continuous wave electromagnetic wave) energy in the radiofrequency (RF) or low frequency (LF) bands.

A suitable generator for this purpose is described in WO 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level.

The generator 102 is connected to an interface joint 106 by an interface cable 104. In the example shown, the interface joint 106 is also connected via a fluid flow line 107 to a fluid delivery device 108, such as a syringe. In some examples, the apparatus may be arranged, additionally or alternatively, to aspirate fluid from the treatment site. In this scenario, the fluid flow line 107 may convey fluid away from the interface joint 106 to a suitable collector (not shown). The aspiration mechanism may be connected at a proximal end of the fluid flow line 107.

If needed, the interface joint 106 can house an instrument control mechanism that is operable by sliding a trigger, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102, fluid delivery device 108 and instrument control mechanism into a single flexible shaft 112, which extends from the distal end of the interface joint 106.

The flexible shaft 112 is insertable through the entire length of an instrument (working) channel of a surgical scoping device 114, which in embodiments of the present invention may comprise an endoscopic ultrasound device.

The surgical scoping device 114 comprises a body 116 having a number of input ports and an output port from which an instrument cord 120 extends. The instrument cord 120 comprises an outer jacket which surrounds a plurality of lumens. The plurality of lumens convey various things from the body 116 to a distal end of the instrument cord 120. One of the plurality of lumens is an instrument channel for receiving the flexible shaft 112. Other lumens may include a channel for conveying optical radiation, e.g. to provide illumination at the distal end or to gather images from the distal end, and an ultrasound signal channel for conveying an ultrasound signal. The body 116 may include an eye piece 122 for viewing the distal end.

An endoscopic ultrasound device typically includes an ultrasound transducer on a distal tip of the instrument cord, beyond an exit aperture of the ultrasound signal channel. Signals from the ultrasound transducer may be conveyed by a suitable cable 126 back along the instrument cord to a processor 124, which can generate images in a known manner. The instrument channel may be shaped within the instrument cord to direct an instrument exiting the instrument channel through the field of view of the ultrasound system, to provide information about the location of the instrument at the target site.

The flexible shaft 112 has a distal assembly 118 (not drawn to scale in FIG. 1) that is shaped to pass through the instrument channel of the surgical scoping device 114 and protrude (e.g. inside the patient) at the distal end of the instrument cord.

The structure of the distal assembly 118 discussed below may be particularly designed for use with an endoscopic ultrasound (EUS) device, whereby the maximum outer diameter of the distal end assembly 118 is equal to or less than 2.0 mm, e.g. less than 1.9 mm (and more preferably less than 1.5 mm) and the length of the flexible shaft 112 can be equal to or greater than 1.2 m.

The body 116 includes a power input port 128 for connecting to the flexible shaft 112. As explained below, a proximal portion of the flexible shaft 112 may comprise a conventional coaxial cable capable of conveying the microwave energy and electroporation energy from the generator 102 to the distal assembly 118.

As discussed above, it is desirable to be able to control the position of at least the distal end of the instrument cord 120. The body 116 may include a control actuator that is mechanically coupled to the distal end of the instrument cord 120 by one or more control wires (not shown), which extend through the instrument cord 120. The control wires may travel within the instrument channel or within their own dedicated channels. The control actuator may be a lever or rotatable knob, or any other known catheter manipulation device. The manipulation of the instrument cord 120 may be software-assisted, e.g. using a virtual three-dimensional map assembled from computer tomography (CT) images.

Figure 2:
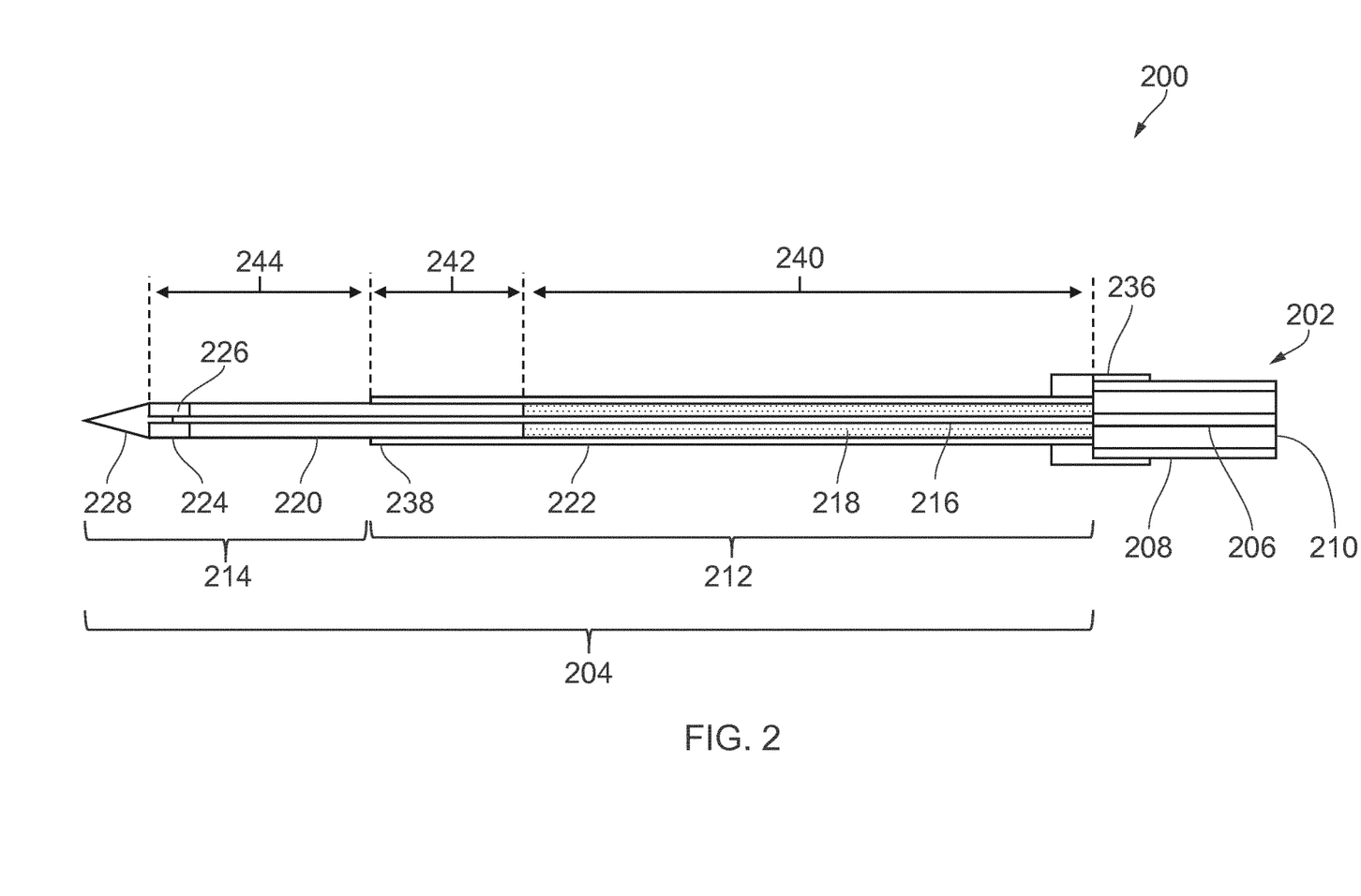
FIG. 2 is a schematic cross-sectional side view of an electrosurgical instrument according to an embodiment of the invention.
Figure 3:
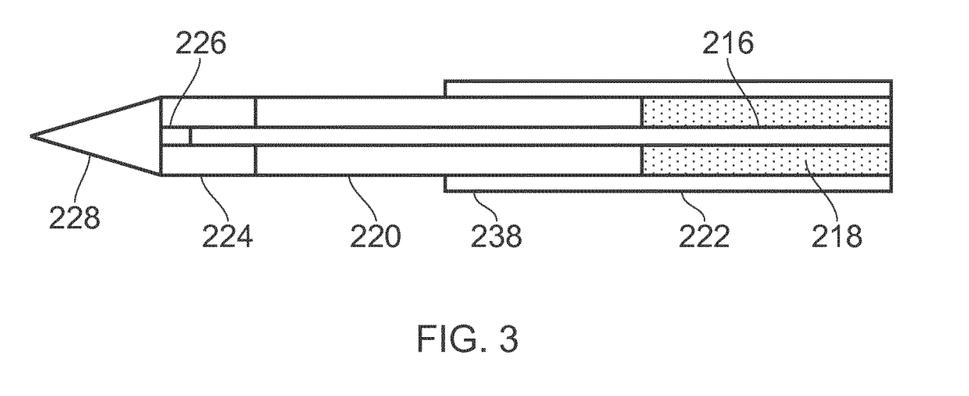
FIG. 3 is a schematic cross-sectional side view of a distal end of the electrosurgical instrument of FIG. 2.

An electrosurgical instrument 200 according to an embodiment of the invention is illustrated in FIGS. 2 and 3. FIG. 2 shows a schematic cross-sectional side view of a distal end of electrosurgical instrument 200 (e.g. corresponding to distal assembly 118 of FIG. 1). FIG. 3 shows an expanded cross-sectional side view of a distal portion of electrosurgical instrument 200.

Electrosurgical instrument 200 includes a flexible coaxial cable 202 and a radiating tip portion 204 mounted at a distal end of the coaxial cable 202. The coaxial cable 202 may be a conventional flexible 50Ω coaxial cable suitable for travelling through the instrument channel of a surgical scoping device. The coaxial cable includes a centre conductor 206 and an outer conductor 208 that are separated by a dielectric material 210. The coaxial cable 202 is connectable at a proximal end, e.g. to generator 102, to receive microwave and/or electroporation energy.

The radiating tip portion 204 includes a proximal coaxial transmission line 212 and a distal needle tip 214 mounted at a distal end of the proximal coaxial transmission line 212. The proximal coaxial transmission line 212 comprises an inner conductor 216 that is electrically connected to the centre conductor 206 of the coaxial cable 202 at the distal end of the coaxial cable 202. The inner conductor 216 has a smaller outer diameter than the centre conductor 206, and is made of a material having a high conductivity, e.g. silver.

The inner conductor 216 is surrounded along a proximal portion thereof by a proximal dielectric sleeve 218. The proximal dielectric sleeve may be made of a flexible insulating material, e.g. PTFE or the like. A distal dielectric sleeve 220 is mounted over a distal portion of the inner conductor 216 to form the radiating tip portion 214. The distal dielectric sleeve 220 is formed of a hard insulating material having a higher rigidity than the proximal dielectric sleeve 218. For example, the distal dielectric sleeve 220 may be made of Zirconia.

The proximal coaxial transmission line 212 is completed by an outer conductor 222 mounted around the proximal dielectric sleeve 218. The outer conductor 222 is formed by a flexible tube of conductive material. The tube is configured to have longitudinal rigidity sufficient to transmit a force capable of penetrating biological tissue (e.g. the duodenum wall) whilst also exhibiting suitable lateral flex to enable the instrument to travel through the instrument channel of a surgical scoping device. The inventors have found that nitinol is a particularly suitable material for the outer conductor 222. The nitinol tube may include a conductive coating, e.g. on its inner surface, in order to reduce transmission losses along the proximal coaxial transmission line 212. This coating may be formed by a material having a higher conductivity that the nitinol, e.g. silver or the like.

The outer conductor 222 overlays a proximal portion of the distal dielectric sleeve 220, to form a distal portion of the proximal coaxial transmission line 212. The region of overlap may be considered as an intermediate coaxial transmission line. As the distal dielectric sleeve 220 has a higher dielectric constant than the proximal dielectric sleeve 218, the region of overlap between the outer conductor 222 and the distal dielectric sleeve 220 enables a physical length of the radiating tip portion 212 to be reduced whilst maintaining a desired electrical length. The length of the overlap between the outer conductor 222 and the distal dielectric sleeve 220 and the dielectric materials of the distal and proximal dielectric sleeves may be selected to obtain a desired electrical length of the radiating tip portion 212.

Figure 4:
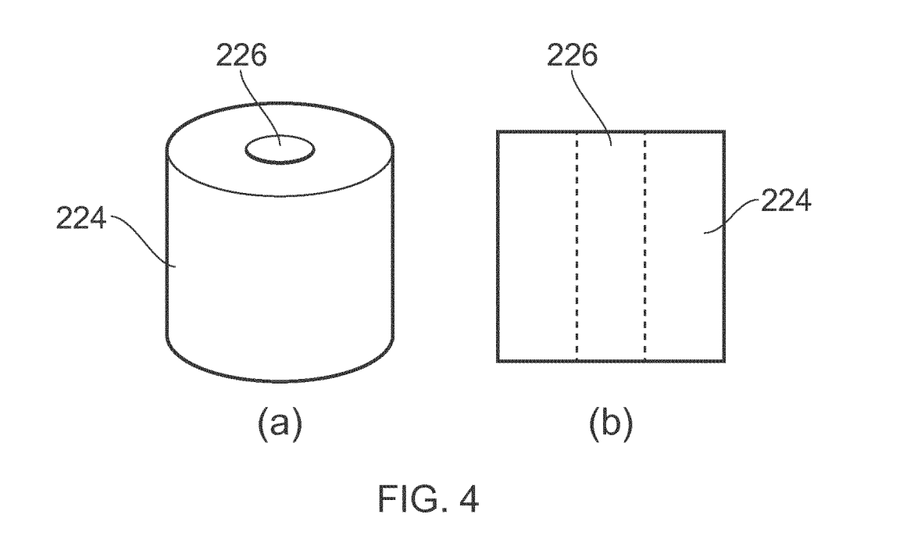
FIG. 4 shows schematic diagrams of an active electrode that may be used in an embodiment of the invention.

The distal needle tip 214 includes an active electrode 224 mounted at a distal end of the inner conductor 216. The active electrode is a cylindrical piece of conductive material (e.g. brass) having a central channel 226 extending therethrough. The active electrode is illustrated in more detail in FIG. 4, which shows a perspective view of the electrode (a) and a cross-sectional side view of the electrode (b). The distal end of the inner conductor 216 protrudes inside the channel 226, where it is electrically connected to the active electrode 224 (e.g. via a soldered or welded connection, or with a conductive adhesive). An outer diameter of the active electrode substantially matches an outer diameter of the distal dielectric sleeve 220, so that the distal needle tip 214 has a smooth outer surface.

Figure 5:
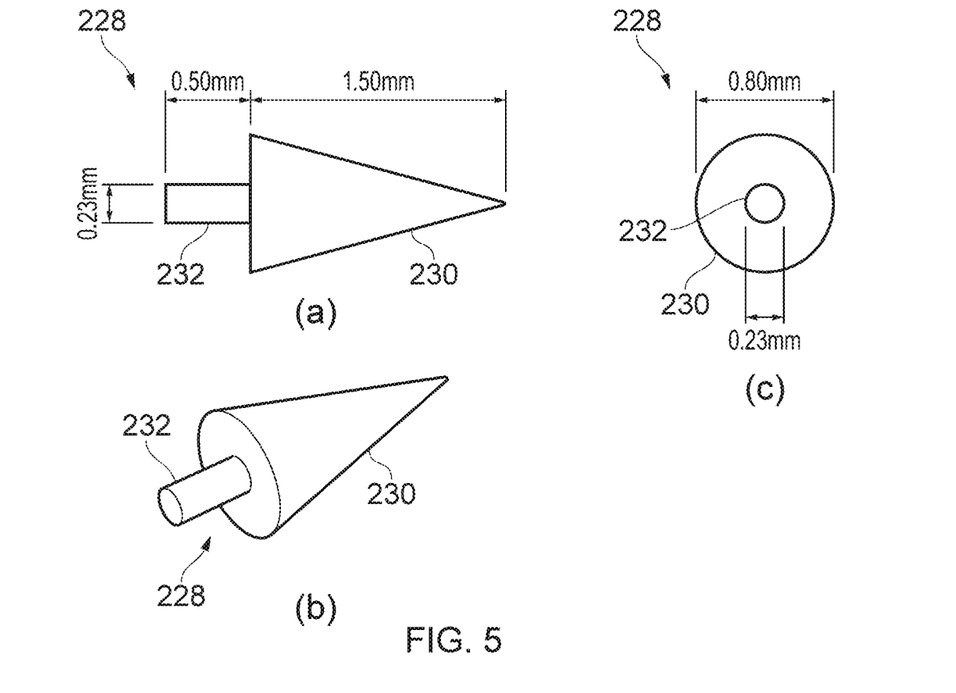
FIG. 5 shows schematic diagrams of a tip element that may be used in an embodiment of the invention.

A pointed tip element 228 is mounted on a distal face of the active electrode 224, to facilitate insertion of the instrument into target tissue. The tip element 228 is preferably made of the same material as the distal dielectric sleeve 220 (e.g. Zirconia). The tip element 228 is shown in more detail in FIG. 5, which shows a side view of the tip element (a), a perspective view of the tip element (b), and a rear view of the tip element (c). Example dimensions of the tip element 228 are shown in FIGS. 5(a) and 5(c). The tip element 228 has a conical body 230 having a protrusion 232 extending from a proximal side thereof. The protrusion 232 is shaped to fit inside the channel 226 in the active electrode 224, to hold the tip element 228 in place. The tip element 228 may be secured to the active electrode 224, e.g. using an adhesive.

Figure 6:
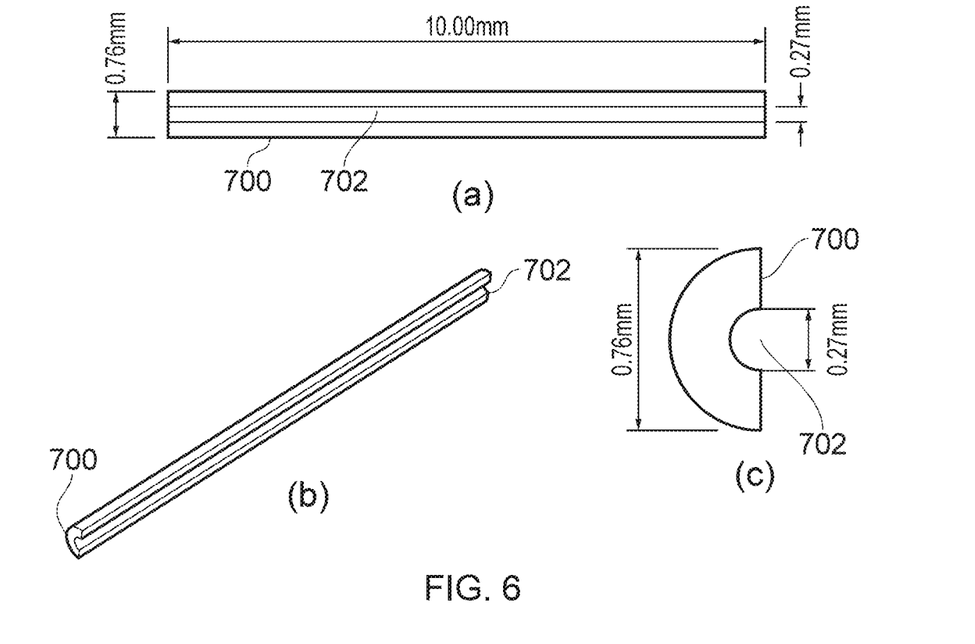
FIG. 6 shows schematic diagrams of a part of a distal dielectric sleeve that may be used in an embodiment of the invention.

The proximal dielectric sleeve 218 and the distal dielectric sleeve 220 may be formed as tubes that slide over the inner conductor 216. In one embodiment, the distal dielectric sleeve 220 may be composed of a pair of cooperating parts which are mounted around the inner conductor 216. FIG. 6 shows an example of a part 700 that may be used to form the distal dielectric sleeve 220. FIG. 6 shows a side view of the part (a), a perspective view of the part (b) and a front view of the part (c). Example dimensions of the part 700 are shown in FIGS. 6(a) and 6(c). The part 700 is a semi-cylindrical piece of rigid dielectric material (e.g. Zirconia) having a longitudinal groove 702 extending along its length. A pair of parts 700 may be assembled together to form the distal dielectric sleeve 220, so that the grooves 702 in each part 700 together form a channel in which the inner conductor 216 is received. The two parts 700 may be secured together, e.g. using an adhesive. Such a structure of the distal dielectric sleeve 220 may facilitate assembly of the radiating tip portion 212. A similar structure comprising a pair of cooperating parts may also be used for the proximal dielectric sleeve 218.

The radiating tip portion 212 is secured to the distal end of the coaxial cable 202 by a collar 236. The collar 236 may act as a radial crimp to secure the radiating tip portion 212 in place. The collar 236 is also arranged to electrically connect the outer conductor 208 of the coaxial cable 202 to the outer conductor 218 of the proximal coaxial transmission line 212. The collar 236 is thus formed from a conductive material, e.g. brass or the like.

Figure 9:
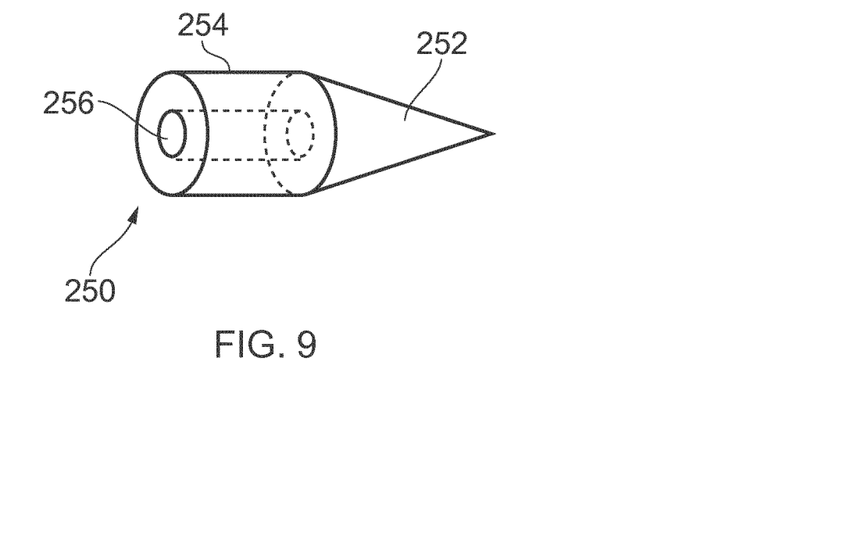
FIG. 9 is a schematic perspective view of another tip element that can be used in the invention.
Figure 10:
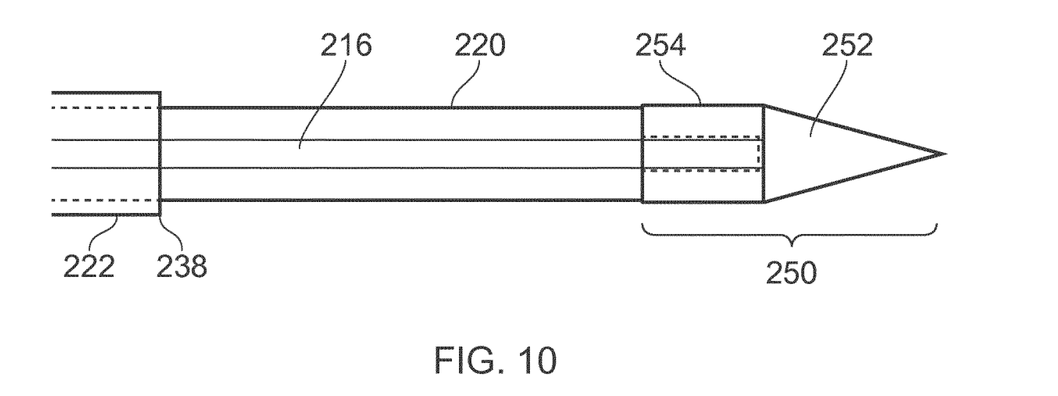
FIG. 10 is a cross-sectional view of a distal tip portion of an instrument that includes the tip element of FIG. 9.

FIGS. 9 and 10 show an alternative arrangement for the distal tip. In this arrangement the pointed tip element and collar are combined in a single tip element 250. The tip element 250 comprises a distal pointed tip 252, e.g. having a conical shape, formed integrally with a proximal cylindrical portion 254 that has a bore 256 therein for receiving a distal portion of the inner conductor 216. The tip element 250 may be fabricated from a single piece of conductive material, such as silver.

In use, microwave energy and energy having an electroporation waveform may be conveyed from the coaxial cable 202 to the radiating tip portion. Energy received from the coaxial cable 202 may be transmitted along the proximal coaxial transmission line 212 to the distal needle tip 214, where it may be delivered to target tissue.

At microwave energies, the distal needle tip 214 is arranged to perform as a half wavelength transformer for delivery of the microwave energy into target tissue. In other words, an electrical length of the distal needle tip 214 may correspond to half a wavelength of the microwave energy. In this manner, microwave energy may be efficiently delivered to target tissue, in order to ablate the target tissue.

The microwave energy may be delivered in pulses in order to minimise heating in the radiating tip portion 212 during microwave ablation. The inventors have found that the energy delivery cycles listed below may enable efficient delivery of microwave energy whilst minimising heating in the radiating tip portion 212, however other energy delivery cycles are also possible:

10 ms microwave energy delivery followed by 90 ms off (i.e. with no microwave energy delivery);
10 ms microwave energy delivery followed by 50 ms off;
10 ms microwave energy delivery followed by 30 ms off;
100 ms microwave energy delivery followed by 900 ms off;
100 ms microwave energy delivery followed by 500 ms off;
100 ms microwave energy delivery followed by 300 ms off;

When electroporation energy is conveyed to the radiating tip portion, an electric field may be set up between the active electrode 224 and a distal portion 238 (distal end) of the outer conductor 222. In this manner, a distalmost edge or end termination of the outer conductor 222 (which may be exposed) may behave as a return electrode for the electroporation energy. The electric field may cause electroporation (e.g. irreversible electroporation) of tissue located around the distal needle tip 214. As the active electrode 224 disposed substantially symmetrically about a longitudinal axis of the instrument, the electric field caused by the electroporation waveform may be axially symmetrical. In other examples, the treatment region may be non-symmetrical, e.g. through suitable configuration of the active electrode.

The electrosurgical instrument 200 is configured for use as an ablation device to deliver microwave and electroporation energy conveyed along the coaxial cable into biological tissue. The electrosurgical instrument 200 is designed in particular to be suitable for insertion through an instrument channel of a surgical scoping device (e.g. an endoscopic ultrasound (EUS) apparatus) to a treatment site. The treatment site may be the pancreas, whereby an instrument cord of the surgical scoping device is inserted into the duodenum, whereupon the electrosurgical instrument 200 is extended to penetrate through the wall of the duodenum into the pancreas to treatment.

The electrosurgical instrument may have several features that render it suitable for use in this context. The radiating tip portion 212 of the instrument desirably has a length equal to or greater than 40 mm with a maximum outer diameter of 1.2 mm. This can ensure the needle is long enough to reach tumours located within the pancreas, and can ensure that the penetration hole is not too large, to facilitate healing.

FIG. 2 shows example dimensions of electrosurgical instrument 200. In a first example, the dimension indicated by reference numeral 240, which corresponds to a length of the proximal dielectric sleeve 218, may be 37.0 mm. The dimension indicated by reference numeral 242, which corresponds to a length of the overlap between the outer conductor 222 and the distal dielectric sleeve 220, may be 4.70 mm. The dimension indicated by reference numeral 244, which corresponds to a distance from the distal end of the outer conductor 222 to the distal end of the active electrode 224, may be 3.00 mm. In a second example, which uses the tip element shown in FIG. 9, the dimension 240 is 37.0 mm, the dimension 242 is 8.30 mm, and the dimension 244 is 5.00 mm.

Figure 7:
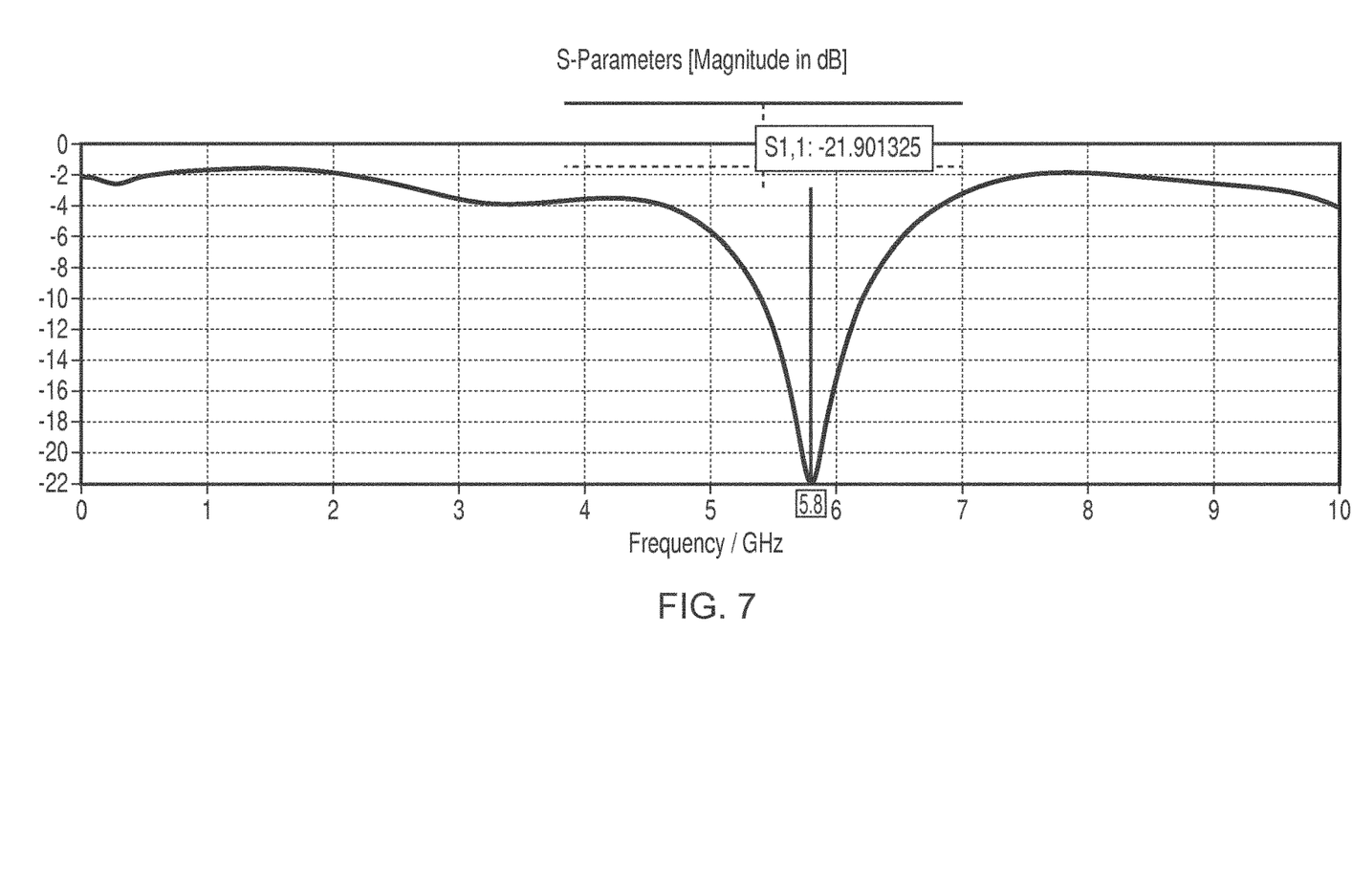
FIG. 7 shows a simulated plot of return loss for a first example of the electrosurgical instrument of FIG. 2.
Figure 11:
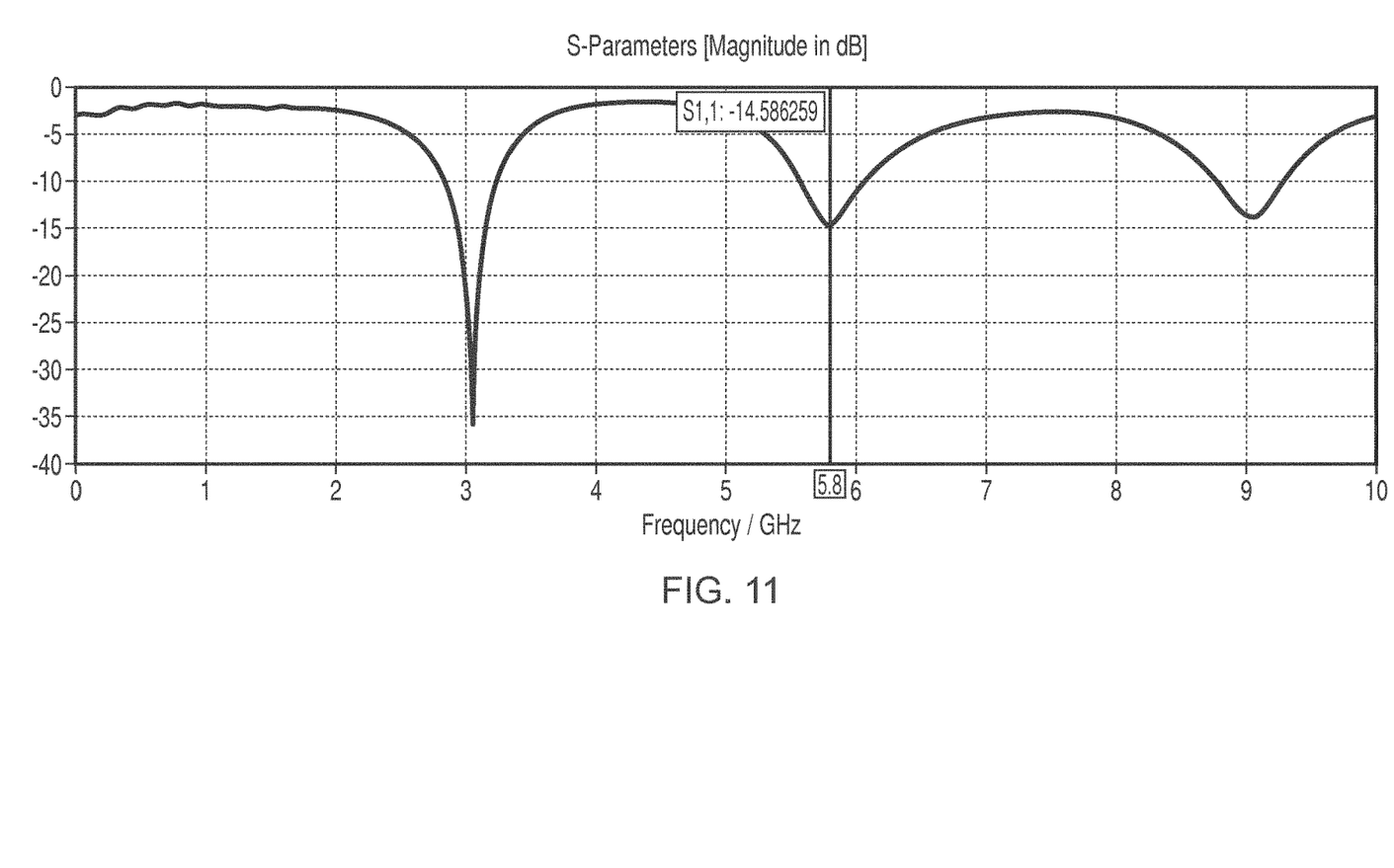
FIG. 11 shows a simulated plot of return loss for a second example of the electrosurgical instrument of FIG. 2.

CST Microwave Studio was used to design and simulate electrosurgical instrument 200 discussed above. FIGS. 7 and 11 shows simulated plots of the S-parameter (also known as the "return loss") against frequency of microwave energy for the first and second examples of the electrosurgical instrument 200 discussed above. As well known in the technical field, the S-parameter is a measure of the return loss of microwave energy due to impedance mismatch, and as such the S-parameter is indicative of the degree of impedance mismatch between the target tissue and the radiating tip portion. The S-parameter can be defined by the equation $P_I = SP_R$, where $P_I$ is the outgoing power in the instrument towards the tissue, $P_R$ is the power reflected back from the tissue, and S is the S-parameter. As shown in FIG. 7, the S-parameter is −21.9 dB at 5.8 GHz, meaning that very little microwave energy was reflected back from the tissue at this frequency (this corresponds to approximately 0.645% of energy being reflected back). This indicates a good impedance match at the operating frequency of 5.8 GHz, and that microwave energy is efficiently delivered from the radiating tip portion into the tissue at this frequency. In FIG. 11, the S-parameter is −14.6 dB at 5.8 GHz.

Figure 8:
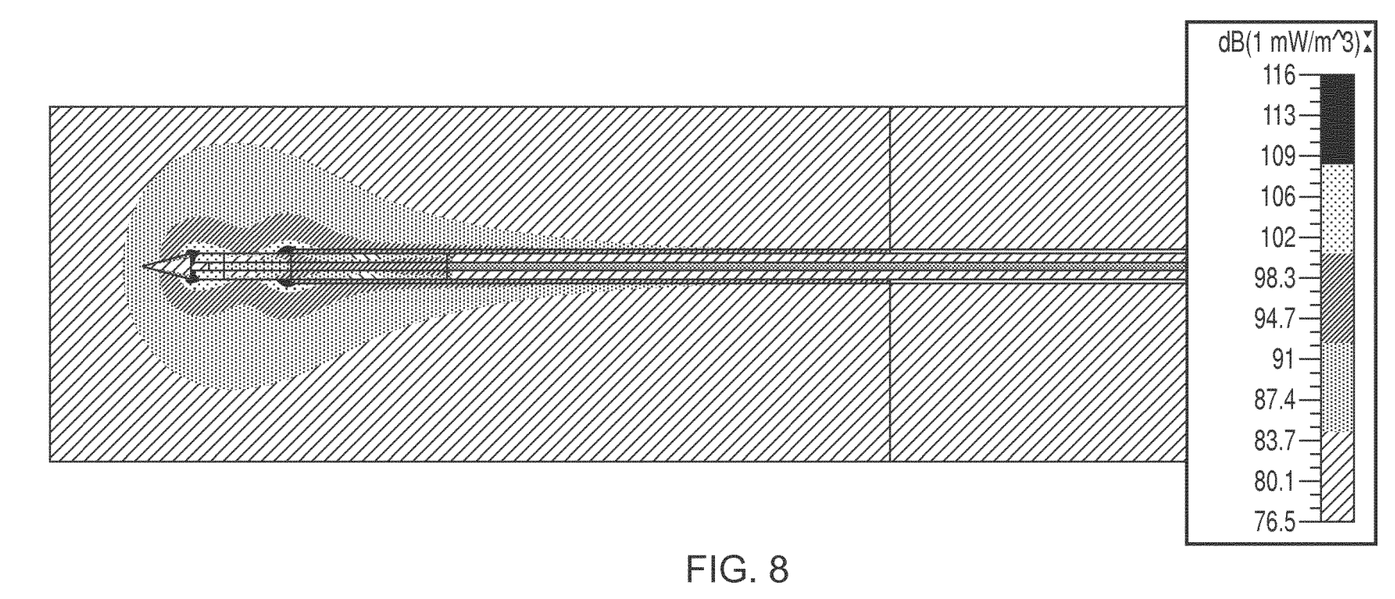
FIG. 8 shows a simulated microwave radiation profile for the first example of the electrosurgical instrument of FIG. 2.
Figure 12:
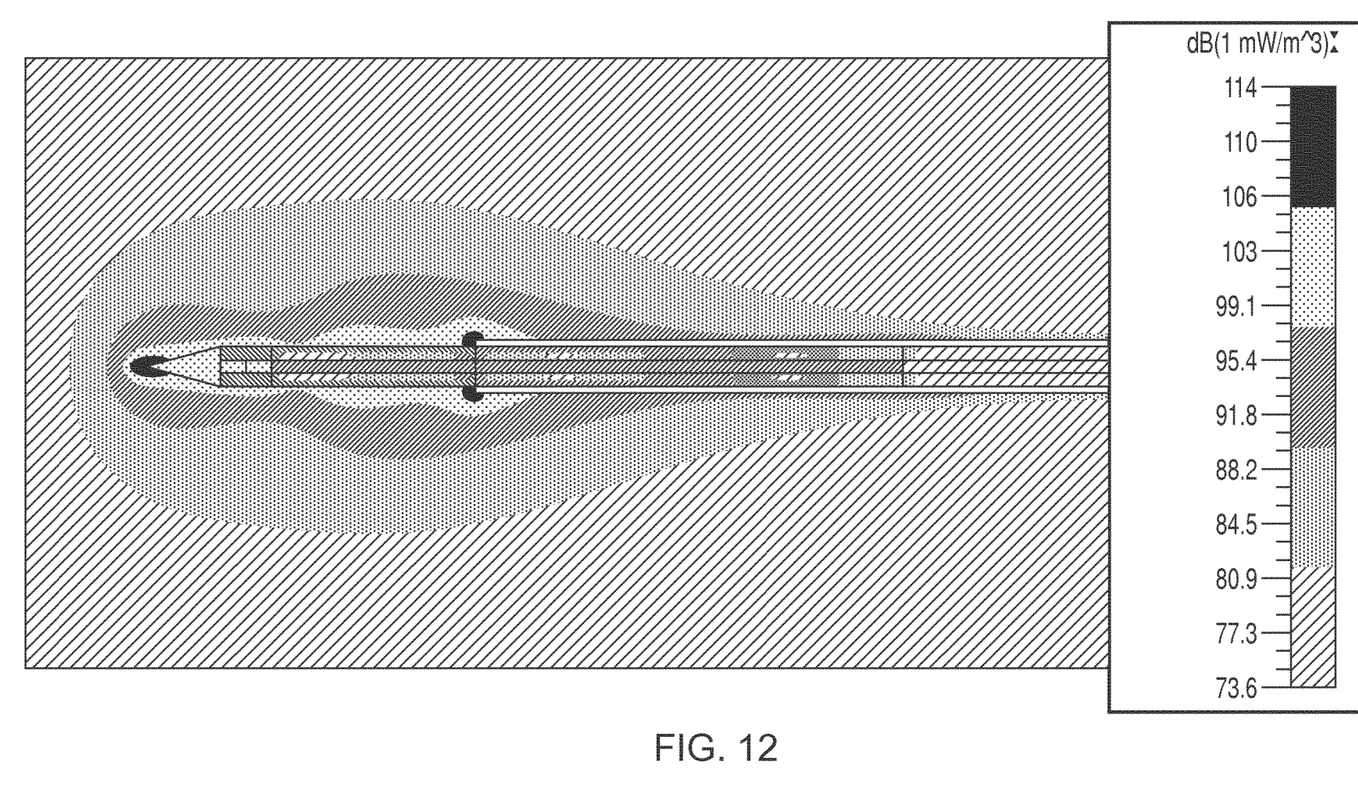
FIG. 12 shows a simulated microwave radiation profile for the second example of the electrosurgical instrument of FIG. 2.

FIGS. 8 and 12 shows calculated radiation profiles in surrounding tissue for the first and second examples of the electrosurgical instrument 200 discussed above. The radiation profile was calculated for an EM energy frequency of 5.8 GHz, using finite element analysis. The calculation shows that microwave energy is radiated around the distal needle tip 214, and gives an indication of the shape of an ablation profile produced by the instrument.

The invention claimed is:
1. An electrosurgical instrument comprising:
a coaxial cable configured to convey microwave energy and an electroporation signal;
a rod-shaped radiating tip portion extending in a longitudinal direction away from a distal end of the coaxial cable, wherein the radiating tip portion comprises:
a proximal coaxial transmission line for receiving and conveying the microwave energy, the proximal coaxial transmission line including an inner conductor, an outer conductor and a dielectric material separating the inner conductor from the outer conductor; and
a distal needle tip mounted at a distal end of the proximal coaxial transmission line, the distal needle tip comprising a rigid dielectric sleeve that extends in the longitudinal direction from a distal end of the proximal coaxial transmission line,
wherein the rod-shaped radiating tip portion has an outer diameter less than an outer diameter of the coaxial cable,
wherein the rigid dielectric sleeve surrounds an elongate conductive element that is electrically connected to the inner conductor of the proximal coaxial transmission line and extends beyond a distal end of the outer conductor of the proximal coaxial transmission line, wherein the elongate conductive element is configured to operate as a half wavelength transformer for the microwave energy to thereby radiate the microwave energy from the distal needle tip into biological tissue,
wherein the elongate conductive element terminates at an active electrode exposed on a distal end of distal needle tip, the elongate conductive element being electrically connected to the active electrode,
wherein the active electrode is axially spaced from a return electrode that is electrically connected to the distal end of the outer conductor of the proximal coaxial transmission line, the active electrode and return electrode being configured to, when the electroporation signal is received by the rod-shaped radiating tip portion, establish an electric field for electroporation of the biological tissue at the distal needle tip, wherein the dielectric material of the proximal coaxial transmission line is more flexible than the rigid dielectric sleeve, and wherein a proximal portion of the rigid dielectric sleeve is contained within a distal portion of the outer conductor.

2. An electrosurgical instrument according to claim 1, wherein the active electrode is a conductive ring arranged concentrically with the elongate conductive element.

3. An electrosurgical instrument according to claim 2, wherein the conductive ring has a channel extending longitudinally therethrough, and wherein a portion of the elongate conductive element is contained within the channel.

4. An electrosurgical instrument according to claim 3, wherein the distal needle tip comprises a tip element mounted at a distal end of the conductive ring to close a distal end of the channel.

5. An electrosurgical instrument according to claim 4, wherein a distal end of the tip element is pointed.

6. An electrosurgical instrument according to claim 1, wherein the rigid dielectric sleeve is made from zirconia.

7. An electrosurgical instrument according to claim 1, wherein the rigid dielectric sleeve is formed by a pair of cooperating parts, each one of the cooperating parts having a longitudinal groove formed in a surface thereof for receiving the elongate conductive element.

8. An electrosurgical instrument according to claim 1, wherein the outer conductor is formed from nitinol.

9. An electrosurgical instrument according to claim 8, wherein a conductive coating is formed on an outer surface of the outer conductor, the conductive coating having a higher conductivity than nitinol.

10. An electrosurgical instrument according to claim 1, wherein the radiating tip portion has a length in the longitudinal direction equal to or greater than 40 mm and up to 100 mm.

11. An electrosurgical instrument according to claim 1, wherein the radiating tip portion has a maximum outer diameter equal to or less than 1.2 mm.

12. An electrosurgical instrument according to claim 1, wherein:

the inner conductor extends from a distal end of the coaxial cable, the inner conductor being electrically connected to a centre conductor of the coaxial cable, and the inner conductor has a diameter that is less than the diameter of the centre conductor of the coaxial cable.

13. An electrosurgical instrument according to claim 1, wherein the coaxial cable is flexible.

14. An electrosurgical instrument according to claim 1, wherein the rod-shaped radiating tip portion includes a non-stick coating along a distal length thereof.

15. An electrosurgical instrument according to claim 14, wherein the non-stick coating is formed from Parylene C or Parylene D.

16. An electrosurgical system for treating biological tissue, the apparatus comprising:

an electrosurgical instrument according to claim 1; and
an electrosurgical generator arranged to supply the microwave energy and the electroporation signal;
wherein the coaxial cable of the electrosurgical instrument is connected to receive the microwave energy and the electroporation signal from the electrosurgical generator.

17. An electrosurgical system according to claim 16 further comprising a surgical scoping device having a flexible insertion cord for insertion into a patient's body, wherein the flexible insertion cord has an instrument channel running along its length, and wherein the electrosurgical instrument is dimensioned to fit within the instrument channel.

18. An electrosurgical system according to claim 16, wherein the electrosurgical generator is configured to supply the electroporation signal, the electroporation signal comprises one or more rapid electromagnetic pulses.

19. An electrosurgical system according to claim 18, wherein each one or more rapid electromagnetic pulses has a pulse width in a range from 1 ns to 10 ms.

20. An electrosurgical system according to claim 19, wherein each pulse has an amplitude in the range 1 kV to 10 kV.

21. An electrosurgical system according to claim 17, wherein the electroporation signal comprises a train of pulses having a duty cycle equal to or less than 50%.

* * * * *